United States Patent
Victor

(12) 
(10) Patent No.: US 6,808,722 B2
(45) Date of Patent: Oct. 26, 2004

(54) METHOD OF USING OPTICALLY-ACTIVATED PARTICLES IN COSMETIC PREPARATIONS

(75) Inventor: Bruce H. Victor, Paterson, NJ (US)

(73) Assignee: Lipo Chemicals, Inc., Paterson, NJ (US)

( * ) Notice: Subject to any disclaimer, the term of this patent is extended or adjusted under 35 U.S.C. 154(b) by 0 days.

(21) Appl. No.: 10/383,363

(22) Filed: Mar. 7, 2003

(65) Prior Publication Data
US 2003/0152537 A1 Aug. 14, 2003

Related U.S. Application Data

(60) Division of application No. 10/095,669, filed on Mar. 12, 2002, now Pat. No. 6,613,359, which is a continuation-in-part of application No. 09/872,648, filed on Jun. 1, 2001, now Pat. No. 6,586,013.

(51) Int. Cl.[7] .................................................. A61K 9/14
(52) U.S. Cl. ........................ 424/489; 424/401; 424/491; 424/59; 424/60; 424/78.03; 514/828; 514/844; 514/846
(58) Field of Search .............................. 424/401, 489, 424/490, 59, 60, 78.03; 514/828, 844, 846

(56) References Cited

U.S. PATENT DOCUMENTS 6,586,013 B2 * 7/2003 Victor ........................ 424/490
6,613,359 B2 * 9/2003 Victor ........................ 424/489

* cited by examiner

*Primary Examiner*—Thurman K. Page
*Assistant Examiner*—Konata M. George
(74) *Attorney, Agent, or Firm*—Ezra Sutton

(57) ABSTRACT

Optically-activated particles for use in cosmetic preparations. The optically-activated particles include a plurality of substrate particles selected from the group consisting of nylons, acrylics, polyesters, other plastic polymers, natural materials, regenerated cellulose, metals and minerals; an optical brightener chemically bonded to each of the plurality of substrate particles to form integral units in the form of optically-activated particles for diffusing light to reduce the visual perception of skin imperfections, including cellulite, shadows, skin discolorations, and wrinkles; and each of the optically-activated particles are encapsulated with a UV transparent coating to increase the diffusion light to further reduce the visual perception of the skin imperfections. The encapsulated optically-activated particles are able to absorb ultraviolet radiation and emit visible light; and the encapsulated optically-activated particles are able to both scatter and absorb light in a diffuse manner in order to reduce the visual perception of skin imperfections, including cellulite, wrinkles, shadows, and skin discolorations, when the optically-activated particles are applied to the skin surface. The encapsulated optically-activated particles are used in the making of cosmetic preparations such as skin lotions, creams, shampoos, body and skin rinses, bath gels, soaps, hair conditioners, color conditioners and rinses, hair color solutions, foundation powders (compressed or loose), tooth pastes, oral rinses, and any acceptable cosmetic vehicle or medium.

29 Claims, 5 Drawing Sheets

METHOD OF USING OPTICALLY-ACTIVATED PARTICLES IN COSMETIC PREPARATIONS

RELATED APPLICATION

This is a divisional application of patent application Ser. No. 10/095,669 filed on Mar. 12, 2002 now U.S. Pat. No. 6,613,359 which is a continuation-in-part of patent application Ser. No. 09/872,648 filed on Jun. 1, 2001 now U.S. Pat. No. 6,586,013.

FIELD OF INVENTION

The present invention relates to optically-activated particles for use in cosmetic preparations to reduce the visual perception of skin imperfections. More particularly, these optically-activated and bonded particles increase the diffusion of light to reduce the visual perception of imperfections including, but not limited to, cellulite, wrinkles, discoloration by veins and arteries, shadows, blotchiness, pores, and follicles. Additionally, these optically-activated and bonded particles reduce the perception of wrinkles around the eyes and mouth, or mild discolorations such as mild scars and blotchiness of the skin in the face area, and can be used in an encapsulated or non-encapsulated form in the formation of various cosmetic preparations selected from the group consisting of skin lotions, creams, shampoos, body and skin rinses, bath gels, soaps, hair conditioners, color conditioners and rinses, hair color solutions, foundation liquids and powders (compressed or loose), tooth pastes and oral rinses, and color cosmetics and skin treatment products.

BACKGROUND OF THE INVENTION

Natural-looking skin is influenced by a number of physiological and genetic factors. Standard definitions of beautiful skin include skin having a transparent quality with uniform undertones of color (i.e. rosy red cheeks). The basis for this natural-looking appearance is in the skin structure itself. The outer layer of human skin is a semi-transparent layer known as the stratum corneum. The transparency of the stratum corneum permits glimpses of the deeper layers of skin, where blood vessels and pigments reside; the reddish hue of the blood vessels' hemoglobin, and the brown/black hue of melanin, the primary skin pigment, combine to produce (what we view as) the skin's color. Of course, in addition to ideal skin having the transparent look with a uniform color distribution, it should also be smooth and even, with no apparent surface flaws. Only a few individuals can ever hope to meet such a standard without some outside assistance. Thus, a wide variety of cosmetics exist to help out where nature has failed.

Although makeup is worn on facial skin, it has not mimicked the actual appearance of natural skin beauty. Currently, the trend for cosmetic preparations have been to more natural-looking make-ups. In particular, one of the long-sought goals has been the development of a foundation that does not give the user a "made-up" look. In reality, however, it is difficult to accomplish the goal of achieving coverage of flaws and unevenness of skin tone, while still maintaining the vibrant look of clean bare skin. This is primarily because those components of makeups which provide the desired color and coverage, such as the titanium or iron oxide pigments, are largely opaque, and therefore obscure that sought-after vibrant transparency. Although in recent years, transparent pigments have become available, the coverage needed to mask flaws in the surface of the skin is frequently lacking.

There remains a need for cosmetic preparations that convey the perception that the user's skin has less wrinkles and less cellulite and less imperfections, obscuring discolorations to the skin and/or reducing skin blotchiness through the use of optically-activated and bonded particles. These optically-activated particles will allow for the emission and reflection of light and increase the diffusion of light to accomplish the foregoing.

DESCRIPTION OF THE PRIOR ART

The use of optical brightener compounds have been disclosed in the prior art. For example, U.S. Pat. No. 4,028,263 to GRAY discloses a bleaching and brightening detergent composition. This water soluble laundry detergent includes an organic anionic detergent, nonionic detergent or mixture thereof, a builder salt, preferably including a silicate, a peroxymonosulfate bleaching agent, a bromide promoter for the bleaching agent and one or more optical brighteners which are stable in the presence of the bleach and the promoter. This prior art patent does not teach or disclose the structure, configuration or composition of the optically-activated and bonded particles for use in cosmetic preparations as disclosed in the present invention.

U.S. Pat. No. 4,752,496 to FELLOWS et al discloses a method of applying cosmetics to a substrate and article. The cosmetics, which are normally dry, are combined with a liquid carrier and film forming agent and deposited onto a substrate. The film forming agent acts to micro encapsulate the cosmetic and lightly bond the cosmetic to the substrate. When the film forming agent dries, it protects the cosmetic. Thus, the cosmetic can be applied to a substrate and covered with a paperboard sheet. This prior art patent does not teach or disclose the structure, configuration or composition of the optically-activated and bonded particles for use in cosmetic preparations as disclosed in the present invention.

U.S. Pat. No. 6,117,435 to PAINTER et al discloses natural look cosmetic compositions. This topical application composition for use on skin includes silica beads having an inner core of silica, a middle layer of metal oxide, and an outer layer of silica; at least one interference pigment; and optionally, at least one non-interference pigment, in a cosmetically or pharmaceutically-acceptable formula. These cosmetic compositions confer a natural appearance to the user's skin, while also reducing the appearance of flaws or defects in the skin without conferring an opaque or made-up appearance. This prior art patent does not teach or disclose the structure, configuration or composition of the optically-activated and bonded particles for use in cosmetic preparations as disclosed in the present invention.

None of the aforementioned prior art patents teach or disclose the use of optically-activated and bonded particles for use in cosmetic preparations. Further, no prior art patents teach or disclose optically-activated particles which are able to both scatter and emit light in a diffuse manner in order to reduce the visual perception of shadows, skin discolorations, wrinkles and cellulite when applied to the skin surface.

Accordingly, it is an object of the present invention to provide optically-activated and bonded particles for use in cosmetic preparations, wherein the optically-activated particles are able to absorb ultraviolet radiation and emit visible light (releases energy in the form of light), and the optically-activated particles are also able to both scatter and emit light in a diffuse manner in order to reduce the visual appearance and perception of skin imperfections, such as shadows, skin discolorations, wrinkles and cellulite when applied to the skin surface.

Another object of the present invention is to provide optically-activated particles in which the substrate (particle) is pre-treated with a swelling agent in order to make the substrate particle wettable, electrostatically and ionically available for bonding, such that the swelling agent treatment of the particles swells the particles and they wet-out to prepare the particles for surface bonding by an optical brightener compound.

Another object of the present invention is to provide optically-activated particles that consist of a pre-treated substrate having an optical brightener compound (surface treatment) being applied and bonded to the substrate, such that the optical brightener compound is one or more molecules thick on the pre-treated substrate.

Another object of the present invention is to provide bonded optically-brightened particles that include an optical brightener compound selected from the group consisting of, but not limited to, Tinopal 5BM, Calcofluor White RC (Stilbene 4), Calcofluor CG (Stilbene 3) and Leucophor BSB Liquid, or equivalents.

Another object of the present invention is to provide optically-activated and bonded particles, having an optical brightener compound being permanently adhered and bonded to the substrate by the function of fixation by Van Der Waal's forces or ionic bonding or covalent bonding which makes the optical brightener compound at least one molecule thick bonded to the pre-treated substrate.

Another object of the present invention is to use optically-activated particles of a size that is below $30\mu$ (microns) (which is below the size that the eye can perceive) in cosmetic applications, wherein the preferred size of the bonded particle is in the range of $5\mu$ to $8\mu$ (microns) in diameter, and preferably the bonded particle is colorless, translucent, and non-visible to the human eye.

Another object of the present invention is to provide optically-activated and bonded particles having a substrate (particle) made of materials selected from the group consisting of nylons, acrylics, polyesters or other plastic polymers, natural materials, regenerated cellulose, metals, minerals or other suitable materials, and have an index of refraction greater than 1 in order that the image of the skin imperfection is bent away from the viewer's visual axis.

Another object of the present invention is to provide optically-activated and bonded particles, wherein the substrate (particle) configuration or structure may be in the form of a spheroid, a cuboid, a cylindrical-shaped particle, a tetrahedroid (pyramidally-shaped), a rhomboid, a plate, or other polygonal shaped configurations; and additionally, these particles may be solid or hollow in structure.

Another object of the present invention is to provide optically-activated particles that may be encapsulated with a UV transparent coating, such as, but not limited to, polyoxymethylene urea (PMU), wherein each capsule acts as a diffusion lens which increases the diffusion of emitted and reflected light to reduce the visual perception of skin imperfections, including cellulite, wrinkles, skin discolorations, and shadows when applied to the skin surface.

Another object of the present invention is to provide optically-activated particles that can be used in an encapsulated or non-encapsulated form in the formation of various cosmetic preparations selected from the group consisting of skin lotions, creams, shampoos, body and skin rinses, bath gels, soaps, hair conditioners, color conditioners and rinses, hair color solutions, foundation liquids and powders (compressed or loose), tooth pastes and oral rinses.

Another object of the present invention is to provide optically-activated particles that when used in cosmetic preparations reduce the visual perception of wrinkles (for example, around the eyes, areas of the arms, around the mouth, under the jaw), cellulite, or mild skin discolorations due to mild scars or varicose veins, and blotchiness of the skin as in the face area.

SUMMARY OF THE INVENTION

In accordance with the present invention, there is provided optically-activated particles for use in cosmetic preparations to reduce the visual perception of skin imperfections. The optically-activated particles include a plurality of substrate particles selected from the group consisting of nylons, acrylics, polyesters, other plastic polymers, natural materials, regenerated cellulose, metals and minerals; an optical brightener chemically bonded to each of the plurality of substrate particles to form integral units in the form of optically-activated particles for diffusing and emitting light to reduce the visual perception of cellulite, shadows, skin discolorations and wrinkles; and each of the optically-activated particles may be additionally, but need not be, encapsulated with a UV transparent coating to increase the diffusion of light to further reduce the visual perception of cellulite, shadows, skin discolorations and wrinkles. The encapsulated optically-activated particles are able to absorb ultraviolet radiation and emit visible light; and the encapsulated optically-activated particles are able to both scatter and emit light in a diffuse manner in order to reduce the visual perception of skin imperfections, including shadows, cellulite, wrinkles, and skin discolorations, when the optically-activated particles are applied to the skin surface. The encapsulated optically-activated particles are used in the making of cosmetic preparations such as skin lotions, creams, shampoos, body and skin rinses, bath gels, soaps, hair conditioners, color conditioners and rinses, hair color solutions, foundation liquids and powders (compressed or loose), tooth pastes and oral rinses.

BRIEF DESCRIPTION OF THE DRAWINGS

Further objects, features, and advantages of the present invention will become apparent upon the consideration of the following detailed description of the presently-preferred embodiment when taken in conjunction with the accompanying drawings, wherein.

DETAILED DESCRIPTION OF ONE OF THE PREFERRED EMBODIMENTS

The optically-activated fixed particles 10 for use in cosmetic preparations of the preferred embodiment of the present invention are represented in detail by FIGS. 1 through 6 of the drawings. These optically-activated fixed particles 10 allow for the emission and diffusion of light 40, 41 for the purpose of reducing the visual perception of cellulite, wrinkles, shadows, skin discolorations by veins and arteries, and the obscuring of particular visual imperfections of the skin support surface 14. Further, these optically-activated fixed particles reduce the perception of wrinkles 16 round the eyes and mouth, areas of cellulite, mild discolorations on the skin, such as minor scars or abrasions and blotchiness of the skin, such as occurs in, but not limited to, the face area.

Figure 1:
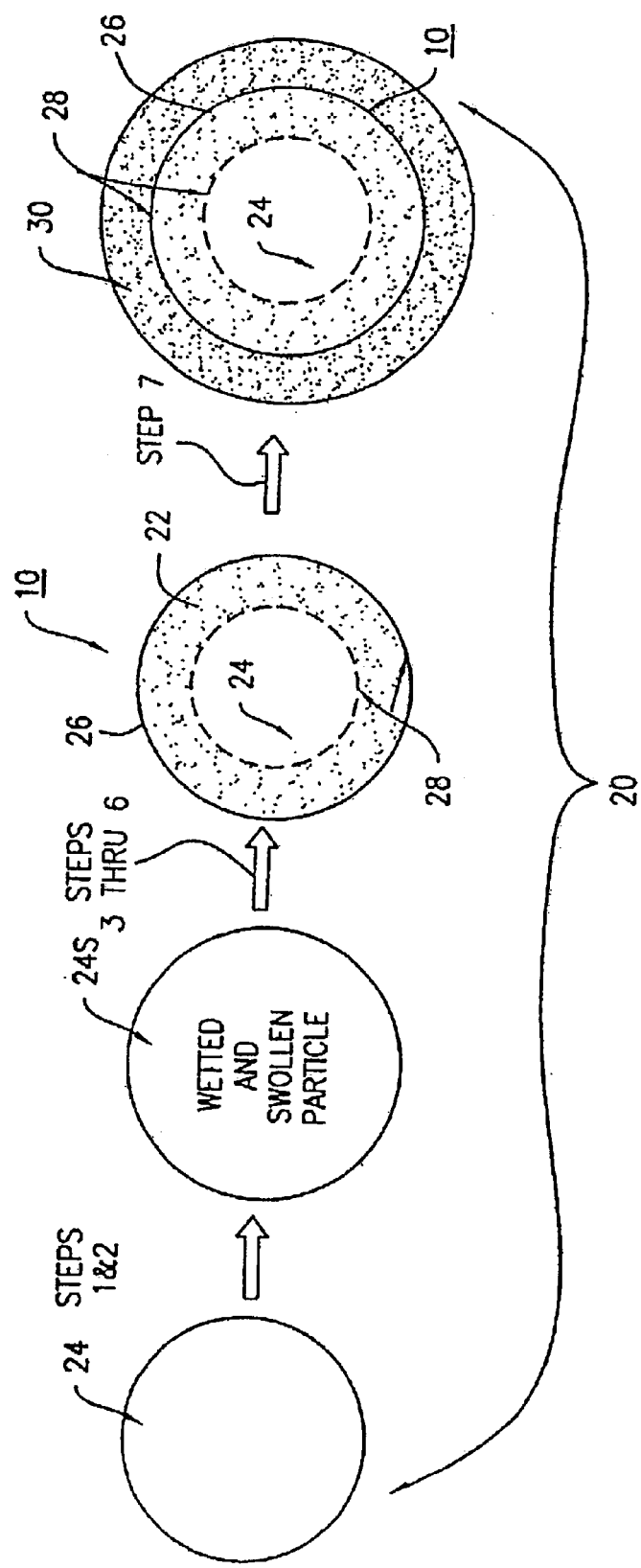
FIG. 1 is a schematic representation of the chemical process of converting a nylon spheroid particle to an encapsulated optically-activated particle with several intervening processing steps.
Figure 3:
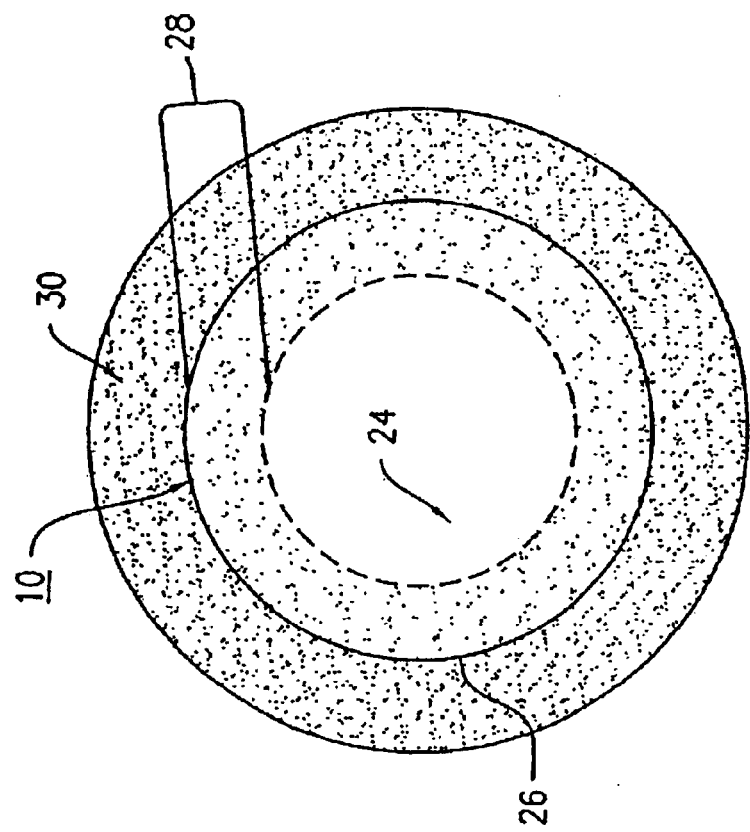
FIG. 3 is an enlarged sectional view of the optically-activated particle of the preferred embodiment of the present invention showing the optically-activated particle encapsulated.
Figure 2:
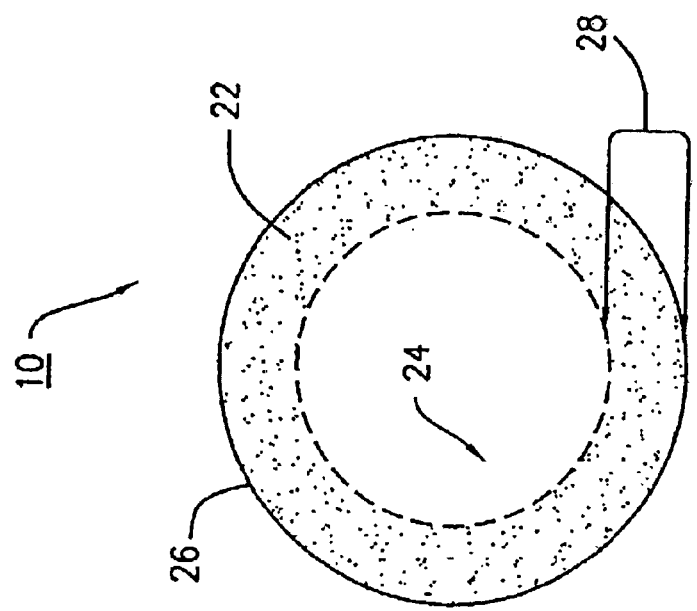
FIG. 2 is an enlarged sectional view of the optically-activated particle of the preferred embodiment of the present invention showing the optical brightener material reacted and bonded within the outermost layers of the nylon spheroid particle.
Figure 4:
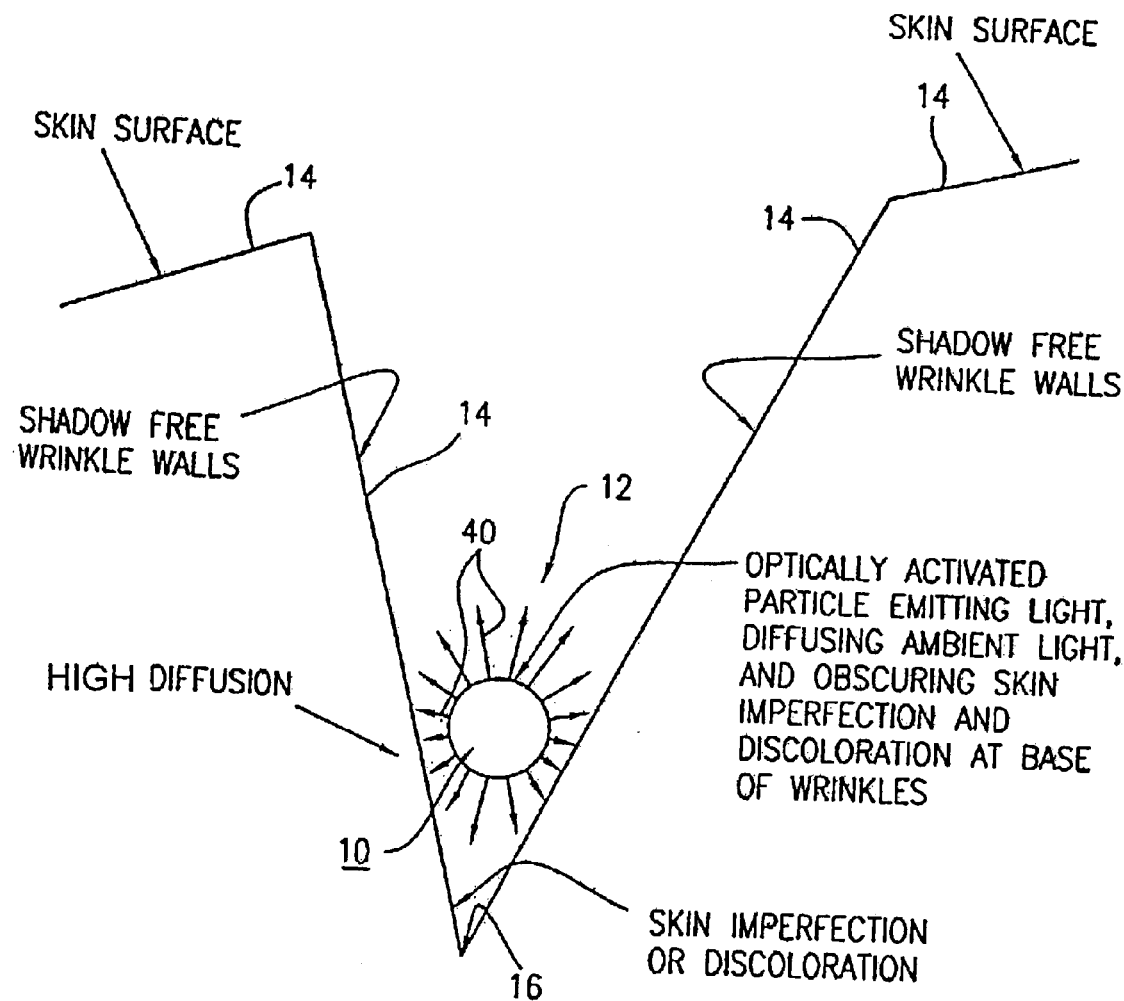
FIG. 4 is an enlarged sectional view of the optically-activated particle of the present invention showing the optically-activated particle within a crease of a user's outer skin layer in which the optically-activated particle is reflecting and emitting light to decrease the shadow effect and any skin imperfection.
Figure 5:
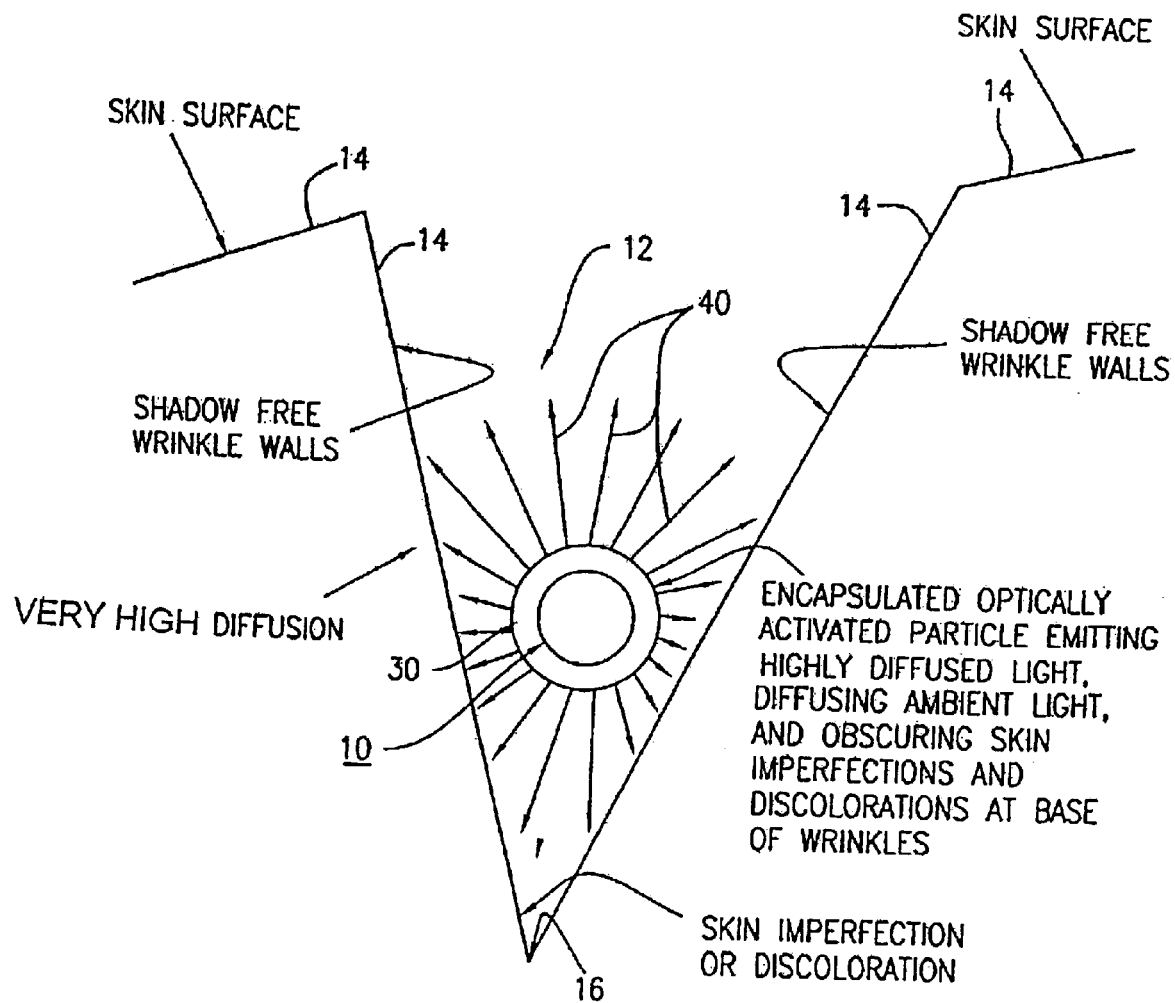
FIG. 5 is an enlarged sectional view of the optically-activated particle of the present invention showing the encapsulated optically-activated particle within a crease of a user's outer skin layer in which the encapsulated optically-activated particle is reflecting and emitting light to further decrease the shadow effect of the skin imperfection.
Figure 6:
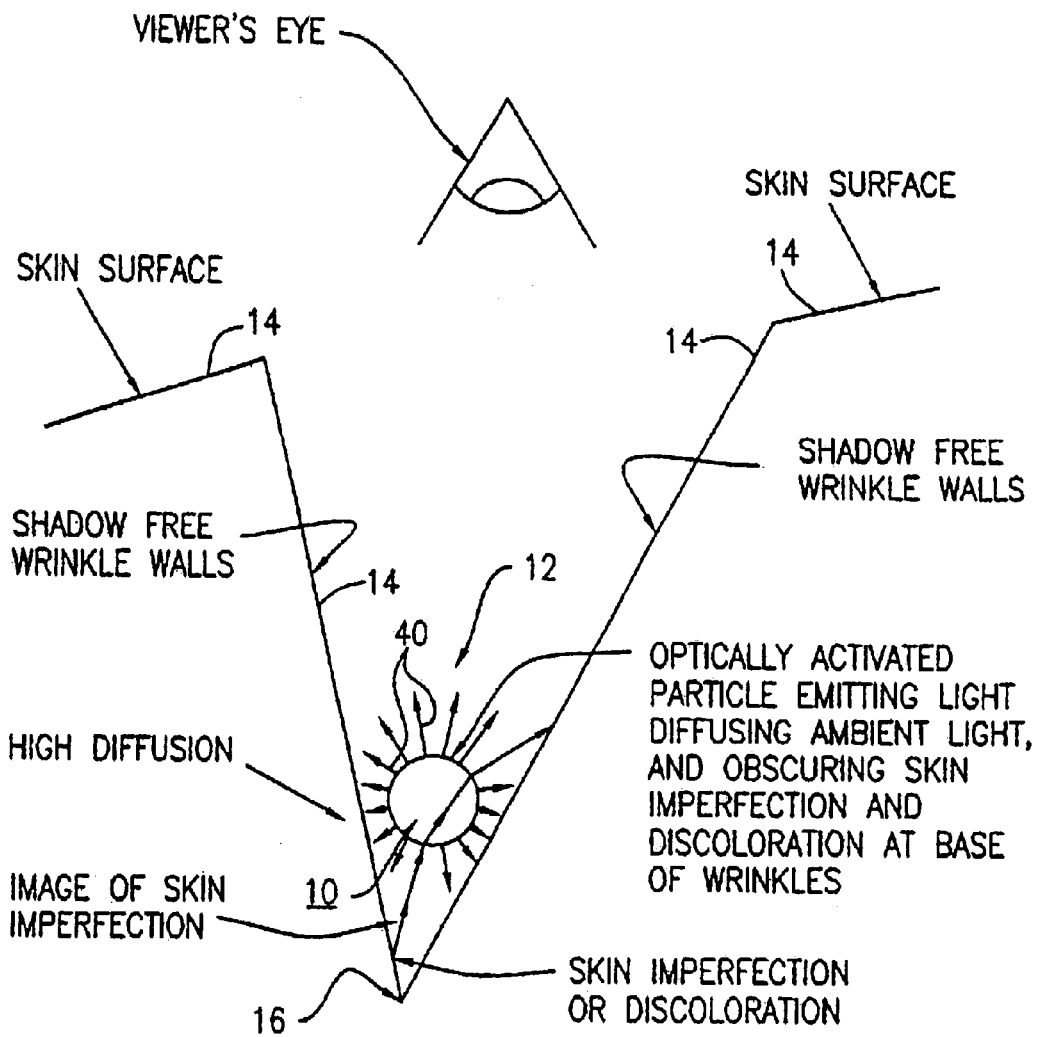
FIG. 6 is an enlarged view showing how the image of the skin imperfection is bent by the optically-activated particle and is not in the viewer's visual axis.

This optically-activated fixed particle 10 and the encapsulated optically fixed particle 12 are created in a chemical process 20, as shown in FIGS. 1 to 3 of the drawings, under heat and/or temperature, and time (t), using a fluorescent compound 22 on a substrate particle 24. The fluorescent compound 22 is fixed to the substrate 24 (i.e., a nylon spheroid particle) by covalent and/or ionic bonding and/or Van der Waals forces and/or hydrogen bonding and/or another strong or weak physio-chemical association such that the fluorescent compound 22 is fixed to the substrate 24 and becomes part of the finished optically-activated fixed particle 10. When using a spheroid as the substrate particle 24, the finished optically-activated fixed particle 10 diffuses light 40, 41 in a radially extending pattern, as shown in FIGS. 4 and 5 of the drawings. The fluorescent compound 22 is fixed to the substrate 24 and a fixed particle 10 is created. The fluorescent compound 22 is difficult to separate or remove from the optically-activated fixed particles 10 that are created. The optically-activated fixed particle 10 may be encapsulated with a transparent or translucent coating 30, such as for example a polyoxymethylene urea (PMU). Thus, the optically-activated fixed particles 10 reduce the visual perception of cellulite, wrinkles, discoloration and shadows when applied the to skin surface 14, as depicted in FIGS. 4 to 6 of the drawings.

The chemical process 20 for making the optically-activated fixed particles 10, as shown in FIG. 1 of the drawings, may include the following examples:

EXAMPLE 1

Propylene glycol (875 g) and PEG 200 (125 g) were added to a 3-L round bottom flask equipped with an overhead stirrer, condenser and heating mantle. Nylon-12 powder was added slowly over 15 min. The mixture was stirred for an additional 15 min, Leucophor B SB solution (Clariant, 50 g) was added and the mixture was stirred at room temperature for 10 min. Distilled water (950 g) was added and the mixture was then slowly heated to 90° C. with a ramp rate of 1–2° C./min. The temperature was held at 90° C. for 30 min., then allowed to cool to room temperature. The mixture was filtered in a Buchner funnel and the white powder was washed with four 1200 mL portions of distilled water and air dried to yield a wet powder which was then dried in an oven at 75° C. for 15 hr to yield a dry white fluorescent powder. Spectrophotometric analysis of the wash solutions indicated that the product contained 0.3% fluorescent compound.

EXAMPLE 2

The procedure from Example 1 was repeated except the reaction temperature was raised to 100° C. Analysis indicated that the product contained 0.4% fluorescent compound.

EXAMPLE 3

The procedure from Example 2 was repeated except nylon-6 powder was used instead of nylon-12 powder. Analysis indicated that the product contained 0.5% fluorescent compound.

EXAMPLE 4

The procedure from example 2 was repeated except ethylene glycol (1000 g) was substituted for the propylene glycol and PEG 200 mixture and no water was added. Analysis indicated that the product contained 0.4% fluorescent compound.

EXAMPLE 5

The procedure from example 2 was repeated except butylene glycol (1000 g) was substituted for the propylene glycol and PEG 200 mixture and no water was added. Analysis indicated that the product contained 0.4% fluorescent compound.

EXAMPLE 6

The procedure from Example 2 was repeated except microcrystalline cellulose powder was used instead of nylon-12 powder. Analysis indicated that the product contained 0.3% fluorescent compound.

EXAMPLE 7

Isopropanol (150 g) was added to a 1-L round bottom flask equipped with an overhead stirrer, condenser and heating mantle. Nylon-12 powder was added slowly over 15 min and the mixture was stirred for an additional 15 min. The mixture was filtered in a Buchner funnel and the filter cake containing approximately 80 g of isopropanol and the nylon powder was placed back in the reaction flask. Distilled water (312 g) and Leucophor BSB solution (Clariant, 8 g) was added and the mixture was stirred at room temperature for 10 min. The mixture was heated to 88° C. for 30 min., then allowed to cool to room temperature. The mixture was filtered in a Buchner funnel and the white powder was washed with four 200 mL portions of distilled water and air dried to yield a wet powder which was then dried in an oven at 75° C. for 15 hr to yield a dry white fluorescent powder. Spectrophotometric analysis of the wash solutions indicated that the product contained 0.3% fluorescent compound.

EXAMPLE 8

The fluorescent powder of from Example 1 was encapsulated as follows. A pre-polymer mixture was prepared by mixing 37% formalin (108.1 g), urea (40 g) and triethanolamine (1.2 g) and heating to 70–75° C. for 2.5 hours. De-ionized water (331.9 g), sodium chloride (48.6 g) and the pre-polymer mixture was then added to a 1000 mL glass beaker equipped with an immersion homogenizer. The mixture was held at 25° C. using a cooling bath and homogenization was begun. The fluorescent powder from Example 1 was then added and the homogenization continued until the powder was dispersed. The pH was then adjusted to 5.0 with aqueous HCl and the homogenization continued for 15 min. The pH was then adjusted to 3.6 for 60 min, 3.0 for 60 min, and 2.2 for 30 min. The mixture was then stirred overnight. The pH was then adjusted to 7.0 (NaOH) and the mixture heated to 60° C. for 60 min. The mixture was then filtered on a Buchner funnel, washed with water, and dried at 50–80° C. to yield a fluorescent powder.

EXAMPLE 9

A skin cream containing the optically-activated fixed particles of the invention was prepared according to the following procedure:

| SEQ | PERCENT | INGREDIENT | INCI NAME |
|---|---|---|---|
| 1 | 77.15 | Deionized Water | Water |
| 1 | 1.00 | Uniphen P-23 | Phenoxyethanol (and) Methylparaben (and) Ethylparaben (and) Propylparaben (and) Butylparaben - |
| 1 | 0.35 | Keltrol CG | Xanthan Gum |
| 2 | 4.00 | Lipovol SES | Sesame (Sesamum Indicum) Oil |
| 2 | 0.50 | Lipopeg 6000DS | PEG-150 Distearate |
| 2 | 1.25 | Lipocol C | Cetyl Alcohol |
| 2 | 2.50 | Liponate CG | Caprylic/Capric Triglyceride |
| 2 | 0.75 | Lipowax P | Cetearyl Alcohol (and) Polysorbate 60 |
| 2 | 2.50 | Lipo GMS 450 | Glyceryl Stearate |
| 3 | 10.00 | Optically Activated Fixed Particles | |

Procedure

1. In main beaker, heat sequence #1 ingredients to 78–80° C. with high sheer propeller mixing at medium/high speed.

2. In separate beaker, combine sequence #2 ingredients and heat to 80° C.

4. Add combined sequences #2 to sequence #1 with medium/high speed high sheer propeller mixing. Continue mixing for 5 minutes or until emulsification is complete.

5. Cool to 25° C.

6. Add sequence #3 and mix until blended.

EXAMPLE 10

A skin cream was prepared as in Example 7 except Encapsulated Optically Activated Fixed Particles were used instead of Optically Activated Fixed Particles.

EXAMPLE 11

A skin cream was prepared as in Example 7 except a mixture of Encapsulated Optically-Activated Fixed Particles and Optically-Activated Fixed Particles were used instead of Optically-Activated Fixed Particles alone.

EXAMPLE 12

A skin gel containing the optically-activated fixed particles of the invention was prepared according to the following procedure:

| SEQ | PERCENT | INGREDIENT | INCI NAME |
|---|---|---|---|
| 1 | 43.80 | Deionized Water | Water |
| 1 | 0.20 | Methylparaben | Methylparaben |
| 1 | 0.10 | Sequestrene Na4T | Tetrasodium EDTA |
| 2 | 3.00 | Liponic EG-1 | Glycereth-26 |
| 2 | 0.10 | Hypan SA-100H | Acrylic Acid/ Acrylonitrogens Copolymer |
| 3 | 1.00 | Deionized Water | Water |
| 3 | .50 | TEA, 99% | Triethanolamine |
| 4 | 15.00 | Carbopol 980 (2%) | Carbomer |
| 5 | 10.00 | Zilgel VV | Glycerin (and) Water (and) Sodium Polyacrylate |
| 6 | 1.00 | Deionized Water | Water |
| 6 | 0.30 | Unicide U-13 | Imidazolidinyl Urea |
| 7 | 10.00 | Optically-Activated Fixed Particles | |
| 8 | 1.00 | Hyaluronic acid (1%) | Sodium Hyaluronate |

Procedure

1. Combine sequence #1 ingredients and heat to 80° C. with propeller mixing.

2. Add premixed sequence #2 to sequence #1 holding temperature at 80° C.

3. Add sequence #3 to batch with high speed propeller mixing. Continue mixing until Hypan has completely hydrated.

4. Add sequence #4 to batch and mix until clear and uniform.

5. Begin cooling batch.

6. Add sequence #5 to batch with propeller mixing.

7. At 35° C., add premixed sequence #6 to batch.

8. Add sequence #7 and sequence #8 to batch with high speed mixing. Continue mixing until Liponyl OAP has completely dispersed.

9. Cool to 25° C. and remove from mixer.

OPERATION OF THE PRESENT INVENTION

The optically-activated fixed particles 10, 12 are used in cosmetic preparations to reduce the visual perception of skin imperfections, such as cellulite, shadows, wrinkles and mild skin discolorations such as mild scars, varicose veins, and blotchiness of the skin, such as, but not limited to, the face area. The uniqueness of using these optically-activated fixed particles 10, 12 within a cosmetic preparation is the emission of light 40, 41 for reducing the perception of skin imperfections and for obscuring of the skin below the particle. The particle itself is preferably, but not limited to, being colorless, transparent or translucent, and non-visible to the human eye. Thus, the human eye only sees the combination of scattered and emitted light 40, 41.

In one embodiment of the invention, when the optically-activated fixed particles 10, 12 are exposed to ambient UV light they absorb the UV light as energy, and release light 40, 41, creating a radiant release of light 40, 41, as shown in FIGS. 4 to 6 of the drawings. Thus, the fixing of the fluorescent compound to the substrate particle 24 creates a radiant emissive source of light 40, 41. While not wanting to be limited by theory, it is thought that this light 40, 41 is minuscule, and may not be consciously perceived by the viewer, and is interpreted by the visual center of perception and images (the visual cortex). Thus, particles 10, 12 perform an optical function for the cosmetic product which obscures skin imperfections and reduces the visual perception of skin imperfections. The primary format of the present invention is to use the particles 10, 12 in a cosmetic vehicle.

These particles 10, 12 may be encapsulated in a transparent or translucent capsule 30, such as but not limited to polyoxymethylene urea (PMU). While not wanting to be limited by theory, it is believed that the capsule acts as a diffusion lens increasing the effective diffusion pattern of light 40, 41 which further reduces the visual perception of cellulite, wrinkles, shadows and skin discoloration regardless of the configuration of the skin surface 14. An additional purpose of fixing the fluorescent compound 22 to a substrate 24 (such as nylon spheroids) is to create particles 10, 12 which are non-reactive and inert for use in cosmetic preparations.

ADVANTAGES OF THE PRESENT INVENTION

Accordingly, an advantage of the present invention is that it provides for optically-activated and bonded particles for use in cosmetic preparations, wherein the optically-activated particles are able to absorb ultraviolet radiation and emit visible light (releases energy in the form of light), and the optically-activated particles are also able to scatter both incident and emitted light in a diffuse manner in order to reduce the appearance and visual perception of skin imperfections, including shadows, skin discolorations, wrinkles, and cellulite, when applied to the skin surface, as well as obscure the skin beneath the particles.

Another advantage of the present invention is that it provides for optically-activated particles in which the substrate (particle) is pre-treated with swelling agents in order to make the substrate particle water wettable, electrostatic and ionically available for bonding, such that the treatment of the particles swells the particles and they wet-out to prepare the particles for surface bonding by an optical brightener compound.

Another advantage of the present invention is that it provides for optically-activated particles that consist of a pre-treated substrate having an optical brightener compound surface treatment) being applied and bonded to the substrate, such that the optical brightener compound is one or more molecules thick on the pre-treated substrate.

Another advantage of the present invention is that it provides bonded optically-brightened particles that include an optical brightener compound selected from, but not limited to, the group consisting of Tinopal 5BM, Calcofluor White RC (Stilbene 4), Calcofluor CG (Stilbene 3) and Leucophor BSB Liquid, or equivalents.

Another advantage of the present invention is that it provides a substrate of optically-activated and bonded particles, with an optical brightener compound being permanently adhered and bonded to the substrate by the function of fixation by Van Der Waal's forces or ionic bonding or covalent bonding which makes the optical brightener compound at least one molecule thick adherence to the pre-treated substrate.

Another advantage of the present invention is that it uses optically-activated particles of a size that is below $30\mu$ (microns) which is below the size that the eye can perceive, wherein the preferred size of the bonded particle is in the range of $5\mu$ to $8\mu$ (microns) in diameter, and preferably the bonded particle is colorless, translucent, and non-visible to the human eye.

Another advantage of the present invention is that it provides optically-activated and bonded particles, having a substrate (particle) made of materials selected from the group consisting of nylons, acrylics, polyesters or other plastic polymers, natural materials, regenerated cellulose, metals, minerals or other suitable materials, and have an index of refraction greater than 1 in order that the image of the skin imperfection is bent away from the viewer's visual axis.

Another advantage of the present invention is that it provides optically-activated and bonded particles, wherein the substrate (particle) configuration or structure may be in the form of, but not limited to, a spheroid, a cuboid, a cylindrical-shaped particle, a tetrahedroid (pyramidally-shaped), a rhomboid, a plate, or other polygonal shaped configurations; and additionally, these particles may be solid or hollow in structure.

Another advantage of the present invention is that it provides optically-activated particles that may be encapsulated with a UV transparent coating, such as, but not limited to, polyoxymethylene urea (PMU), wherein each capsule acts as a diffusion lens which increases the diffusion of light to reduce the visual perception of skin imperfections, such as cellulite, wrinkles, skin discolorations and shadows when applied to the skin surf ace.

Another advantage of the present invention is that it provides optically-activated particles that can be used in an encapsulated or non-encapsulated form in the formation of various cosmetic preparations selected from the group consisting of skin lotions, creams, shampoos, body and skin rinses, bath gels, soaps, hair conditioners, color conditioners and rinses, hair color solutions, foundation powders (compressed or loose), tooth pastes and oral rinses.

Another advantage of the present invention is that it provides optically-activated particles that when used in cosmetic preparations reduce the visual perception of skin imperfections, such as wrinkles (for example, around the eyes, areas of the arms, around the mouth, under the jaw), cellulite, or mild skin discolorations due to mild scars or varicose veins, and blotchiness of the skin as in the face area.

A latitude of modification, change, and substitution is intended in the foregoing disclosure, and in some instances, some features of the invention will be employed without a corresponding use of other features. Accordingly, it is appropriate that the appended claims be construed broadly and in a manner consistent with the spirit and scope of the invention herein.

What is claimed is:

1. Optically-activated fixed particles far use in cosmetic, toiletries, and pharmaceutical preparations to reduce the visual perception of skin imperfections, comprising:
   a) a plurality of insoluble solid substrate particles; and
   b) a fluorescent compound fixed to each of said plurality of substrate particles to form integral units in the form of optically-activated fixed particles.

2. Optically-activated fixed particles in accordance with claim 1, wherein each of said plurality of substrate particles has a composition selected from the group consisting of nylons, polyamides, polyacrylates, acrylics, polyesters, other plastic polymers, natural materials, regenerated cellulose, metals and minerals, or mixtures of these.

3. Optically-activated fixed particles in accordance with claim 1, wherein each of said plurality of substrate particles is at least $0.1\mu$ (microns) in size, but below $50\mu$ in size.

4. Optically-activated fixed particles in accordance with claim 1, wherein each of said plurality of substrate particles is at last $1.0\mu$ (microns) in size, but below $30\mu$ in size.

5. Optically-activated fixed particles in accordance with claim 1, wherein each of said plurality of substrate particles is at least $2.0\mu$ (microns) in size, but below $15\mu$ in size.

6. Optically-activated fixed particles in accordance with claim 1, wherein each of said plurality of substrate particles has a configuration or structure selected from the group consisting of a spheroid, a cuboid, a cylindrical-shaped particle, a tetrahedroid, a rhomboid, a plate, other polygonal shaped configurations, and irregular shapes.

7. Optically-activated fixed particles in accordance with claim 1, wherein each of said plurality of substrate particles is solid or hollow in structure.

8. Optically-activated particles in accordance with claim 1, wherein said plurality of substrate particles are pre-treated to make said plurality of substrate particles water wettable and/or swollen and/or electrostatic and ionically available, wherein said plurality of pre-treated substrate particles are ready for fixation by said fluorescent compound.

9. Optically-activated fixed particles in accordance with claim 1, wherein said fluorescent compound is fixed to said plurality of substrate particles by ionic, covalent, or hydrogen bonding.

10. Optically-activated fixed particles in accordance with claim 1, wherein said fluorescent compound is fixed to said plurality of substrate particles by Van der Waals forces, or by strong or weak physio-chemical association.

11. Optically-activated fixed particles in accordance with claim 1, wherein said fluorescent compound is selected from the group consisting of derivatives of stilbene 4,4' diaminostilbene, bipehenyl, heterocycles, or any other fluorescent materials such as Tinopal 5BM, Calcofluor White RC (Stilbene 4), Calcofluor CG (Stilbene 3), and Leucophor BSB.

12. Optically-activated fixed particles in accordance with claim 1, wherein each of said optically-activated fixed particles is colorless or translucent or transparent, and non-visible to the human eye.

13. Optically-activated fixed particles in accordance with claim 1, wherein each of said optically-activated fixed particles has a configuration or structure selected from consisting of a spheroid, a cuboid, a cylindrical-shaped particle, a tetrahedroid, a rhomboid, a plate, other polygonal shaped or irregular shaped configurations.

14. Optically-activated fixed particles in accordance with claim 1, wherein each of said optically-activated particles is solid or hollow in structure.

15. Optically-activated fixed particles in accordance with claim 1, wherein each of said optically-activated fixed particles is a polyamide-based solid.

16. Optically-activated fixed particles in accordance with claim 1, wherein said optically-activated fixed particles are used in the making of cosmetics, toiletries and pharmaceutical preparations selected front the group consisting of skin lotions, creams, shampoos, body and skin rinse, bath gels, soaps, hair conditioners, color conditioners and rinses, hair color solutions, foundation liquids and powders (compressed or loose), tooth pastes, oral rinses, color cosmetics, and skin treatment products.

17. Optically-activated fixed particles in accordance with claim 1, wherein said optically-activated fixed particles both scatter and emit light in a diffuse manner to reduce the visual perception of skin imperfections when said optically-activated fixed particles are applied to the skin surface.

18. Optically-activated fixed particles in accordance with claim 1, wherein said optically-activated fixed particles absorb ultraviolet light and emit visible light.

19. Optically-activated fixed particles in accordance with claim 1, wherein said optically-activated fixed particles absorb visible light at certain wavelengths and emit visible light at longer wavelengths.

20. Optically-activated particles in accordance with claim 1, further includes a transparent and/or translucent coating selected from the group consisting of polyoxymethylene urea, polyoxymethylene, melamine, PVA, PCV, polyacrylates, polymethacrylates, polyvinyls, plastic polymers, organic or inorganic gels, natural or synthetic gelatins, wherein said coating forms a capsule and each capsule acts as an extra diffusing interface of emitted light, thereby increasing the diffusion of emitted and reflected light, or reducing the visual perception of skin imperfections when applied to the skin surface.

21. Optically-activated fixed particles in accordance with claim 1, wherein each of said encapsulated optically-activated fixed particles is a polyamide-based solid for enhancing the radial diffusing of light from each of said encapsulated optically-activated fixed particles to reduce the visual perception of skin imperfections.

22. Optically-activated fixed particles in accordance with claim 1, further including encapsulated optically-activated particles having a size in the range of $0.1\mu$ to $50\mu$ (microns).

23. Optically-activated fixed particles in accordance with claim 1, further including encapsulated optically-activate particles having a size in the range of $1\mu$ to $30\mu$ (microns).

24. Optically-activated fixed particles in accordance with claim 1, further including encapsulated optically-activated particles having a size in the range of $2\mu$ to $15\mu$ (microns).

25. Optically-activated fixed particles in accordance with claim 1, further including encapsulated optically-activated fixed particles used in the making of cosmetics, toiletries, and pharmaceutical preparations selected from the group consisting of skin lotions, creams, shampoos, body and skin rinses, bath gels, soaps, hair conditioners, color conditioners and rinses, hair color solutions, foundation liquids and powders (compressed or loose), tooth pastes, oral rinses, color cosmetics, skin treatment products, and any cosmetically-acceptable vehicles.

26. Optically-activated fixed particles in accordance with claim 1, further including encapsulated optically-activated fixed particles which absorb light and emit and diffuse light in a diffuse manner to reduce the visual perception of skin imperfections when said encapsulated optically-activated particles are applied to the skin surface.

27. A method of using a composition having optically-activated fixed particles for use in cosmetics, toiletries and pharmaceutical applications in order to reduce the visual perception of skin imperfections, wherein said composition comprises:

a) a plurality of substrate particles selected from the group consisting of polyamides, polyacrylates, polyesters, other plastic polymers, natural materials, regenerated cellulose, cellulose, starch, metals, salts, minerals, and other insoluble solids;

b) a fluorescent compound fixed to each of said plurality of substrate particles to form integral units in the form of optically-activated fixed particles for emitting and diffusing light to reduce the visual perception of skin imperfections, including shadows, skin discolorations, cellulite, wrinkles, and mild scars; and c) said method comprising the step of applying said composition to a person's skin to reduce the visual perception of skin imperfections by using said optically-activated fixed particles to emit and diffuse light.

28. Optically-activated particles in accordance with claim 1, wherein said skin imperfections include shadows, skin discolorations, cellulite, open pores, mild scars, hair follicles and blotchiness.

29. A method of making optically-activated particles in accordance with claim 27, wherein said skin imperfections includes shadows, skin discolorations, cellulite, wrinkles, open pores, mild scars, hair follicles and blotchiness.

* * * * *